US010238270B2

(12) United States Patent
Araki

(10) Patent No.: US 10,238,270 B2
(45) Date of Patent: Mar. 26, 2019

(54) FLEXIBLE TUBE, AND INSERTION DEVICE AND ENDOSCOPE EMPLOYING THE FLEXIBLE TUBE

(71) Applicant: OLYMPUS CORPORATION, Hachioji-shi, Tokyo (JP)

(72) Inventor: Kohei Araki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/783,425

(22) Filed: Oct. 13, 2017

(65) Prior Publication Data

US 2018/0042458 A1 Feb. 15, 2018

Related U.S. Application Data

(63) Continuation of application No. PCT/JP2016/062128, filed on Apr. 15, 2016.

(30) Foreign Application Priority Data

May 18, 2015 (JP) ................................. 2015-101183

(51) Int. Cl.
*A61B 1/005* (2006.01)
*A61B 1/01* (2006.01)
(Continued)

(52) U.S. Cl.
CPC .............. *A61B 1/0055* (2013.01); *A61B 1/00* (2013.01); *A61B 1/00002* (2013.01); *A61B 1/01* (2013.01); *G02B 23/24* (2013.01); *A61B 1/00163* (2013.01)

(58) Field of Classification Search
CPC ............ A61B 1/00064; A61B 1/00078; A61B 1/0055; A61M 25/0053; A61M 25/0054;
(Continued)

(56) References Cited

U.S. PATENT DOCUMENTS 4,549,542 A * 10/1985 Chien .................. A62B 18/045
128/201.24
2009/0023989 A1* 1/2009 Honda ................ A61B 1/00133
600/106
(Continued)

FOREIGN PATENT DOCUMENTS

JP H01-112801 U 7/1989
JP H05-323205 A 12/1993
(Continued)

OTHER PUBLICATIONS

Nov. 30, 2017 International Preliminary Report on Patentability issued in International Patent Application No. PCT/JP2016/062128.
(Continued)

Primary Examiner — Ryan Henderson
Assistant Examiner — Aaron B Fairchild
(74) Attorney, Agent, or Firm — Oliff PLC

(57) ABSTRACT

The flexible tube includes a plurality of spiral tubes fitted with each other, and each spiral tube is formed by winding a band-like element and includes a densely wound portion and a loosely wound portion. The loosely wound portion of a first spiral tube is covered with the densely wound portion of a second spiral tube, so that the flexible tube has uniform hardness and resiliency. The flexible tube is suitably applied to an insertion device.

7 Claims, 9 Drawing Sheets

(51) Int. Cl.
*A61B 1/00* (2006.01)
*G02B 23/24* (2006.01)

(58) Field of Classification Search
CPC .. A61M 25/0147; F16L 11/081–11/083; F16L 11/10
See application file for complete search history.

(56) References Cited

U.S. PATENT DOCUMENTS

| | | | | |
|---|---|---|---|---|
| 2010/0280449 A1* | 11/2010 | Alvarez | ........... | A61B 17/00234 604/95.04 |
| 2013/0112457 A1* | 5/2013 | Kitagawa | ............. | A61B 1/0056 174/68.3 |
| 2013/0144126 A1* | 6/2013 | Iede | ..................... | A61B 1/0055 600/139 |
| 2013/0331651 A1* | 12/2013 | Iede | ..................... | A61B 1/0055 600/140 |
| 2014/0155697 A1* | 6/2014 | Iede | ..................... | A61B 1/0055 600/139 |
| 2016/0249786 A1* | 9/2016 | Saito | .................. | G02B 23/2476 600/140 |
| 2016/0249788 A1* | 9/2016 | Saito | .................... | A61B 1/0055 600/140 |
| 2017/0215712 A1* | 8/2017 | Hoshi | ....................... | A61B 1/01 |
| 2017/0254447 A1* | 9/2017 | Saito | ....................... | F16L 11/10 |
| 2017/0261136 A1* | 9/2017 | Saito | ....................... | F16L 11/10 |
| 2017/0265720 A1* | 9/2017 | Saito | .................... | A61B 1/0057 |

FOREIGN PATENT DOCUMENTS

| | | |
|---|---|---|
| JP | H06-23501 U | 3/1994 |
| JP | 2013-097327 A | 5/2013 |

OTHER PUBLICATIONS

Dec. 20, 2016 Office Action issued in Japanese Patent Application No. 2016-564104.

May 17, 2016 Search Report issued in International Patent Application No. PCT/JP2016/062128.

\* cited by examiner

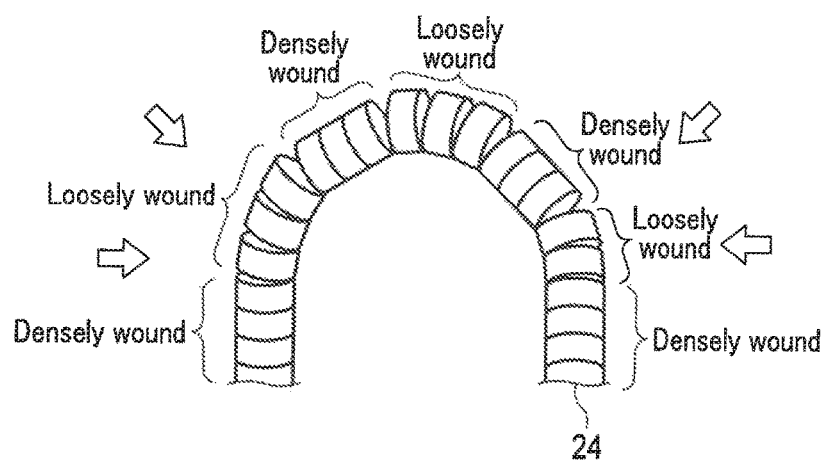
F I G. 5A
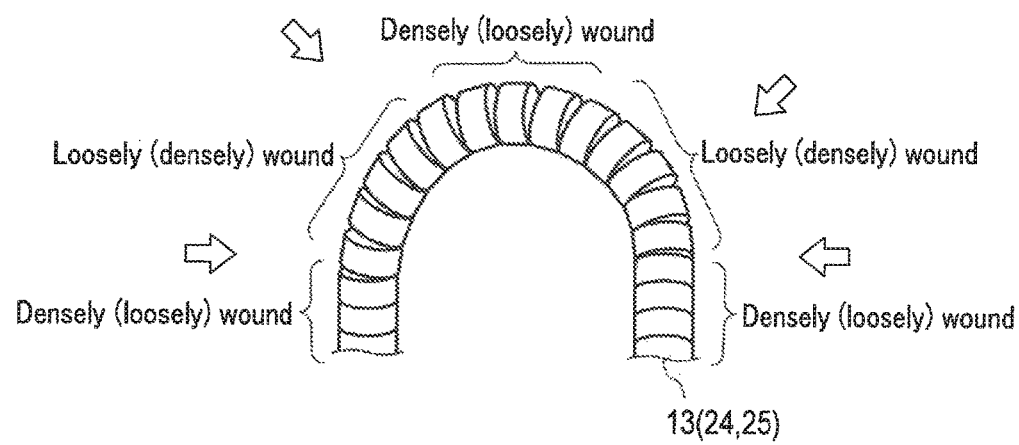
F I G. 5B

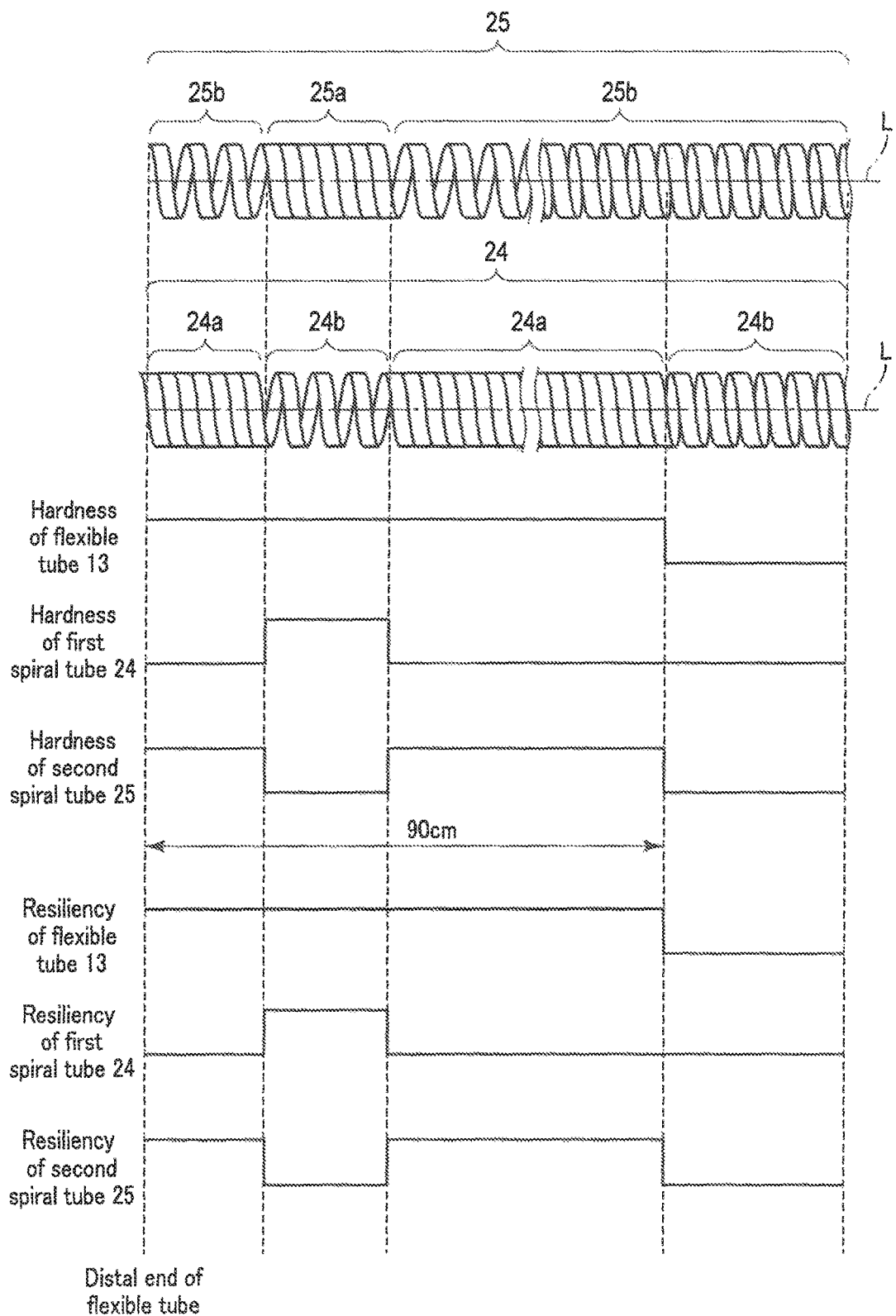
F I G. 9

FLEXIBLE TUBE, AND INSERTION DEVICE AND ENDOSCOPE EMPLOYING THE FLEXIBLE TUBE

CROSS-REFERENCE TO RELATED APPLICATIONS

This is a Continuation Application of PCT Application No. PCT/JP2016/062128, filed Apr. 15, 2016, which was published under PCT Article 21(2) in Japanese.

This application is based upon and claims the benefit of priority from prior Japanese Patent Application No. 2015-101183, filed May 18, 2015 the entire contents of which are incorporated herein by reference.

BACKGROUND OF THE INVENTION

1. Field of the Invention

The present invention relates to a flexible tube which is used for an insertion section, is bendable with a uniform curvature and has such resilient property as ensures reliable insertion property. The present invention also relates to an insertion device and an endoscope including such the flexible tube.

2. Description of the Related Art

In general, a long insertion section of an endoscope is inserted into a body cavity or a lumen having a number of flexures. The insertion section includes a distal end portion which is the distal side of the insertion section, a bendable portion continuous with the proximal side of the distal end portion, and a flexible tube continuous with the bendable portion and connected to an operation section. At least an imaging optical system is incorporated in the distal end portion.

The bendable portion is made of a plurality of annular members coupled to joints, and is actively bent by means of wires. The flexible tube follows the bendable portion at the time of insertion, bends in accordance with the flexures of the lumen, and transmits a propulsion force to the inserted distal end portion. The flexible tube of the insertion section has a laminated structure including a spiral tube, a reticulated tube which covers the spiral tube, and an outer sheath which is a tube made of an elastic material such as rubber or thermoplastic elastomer.

As the spiral tube of a flexible tube, Jpn. Pat. Appln. KOKAI Publication No. 2013-097327 describes a structure in which a densely wound portion (a closely wound portion) and a loosely wound portion are alternately arranged. The densely wound portion is a portion where a band-like element wire is spirally wound with its adjacent turns in tight contact with each other, and the loosely wound portion is a portion where the element wire is spirally wound with its adjacent turns away from each other by a predetermined distance. Since the loosely wound portion and the densely wound portion (which is under initial tension) are arranged as above in the spiral tube, the flexible tube does not bend and maintains a straight state when a small load is applied thereto, but bends largely when it comes into contact with a flexure of the large intestine. Accordingly, a large tension is not applied to the intestine, and the patient does not feel much discomfort. Since the densely wound portion is under initial tension, the flexible tube has proper resilient property and returns to the straight state when it is relieved of a load.

BRIEF SUMMARY OF THE INVENTION

According to an embodiment of the present invention, there is provided a flexible tube comprising: a plurality of spiral tubes overlaid and fitted with one another, with central axes along a common line, each of the spiral tubes being formed by spirally winding an element wire, the spiral tubes including a first spiral tube and a second spiral tube, each of the first spiral tube and the second spiral tube including at least one densely wound portion and a loosely wound portion located at least at one end of the densely wound portion, and the loosely wound portion of the first spiral tube being overlaid and fitted with the densely wound portion of the second spiral tube.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5A is a view showing the first spiral tube and second spiral tube of the first embodiment bend.

FIG. 5B is a view showing the first spiral tube and second spiral tube bend when they are fitted with each other.

FIG. 9 is a view showing the positional relationships between a side face of a first spiral tube and a side face of a second spiral tube are in a flexible tube of the third embodiment, and also illustrates relationships between the hardness and resiliency of the flexible tube and the hardness and resiliency of each spiral tube.

DETAILED DESCRIPTION OF THE INVENTION

Hereinafter, embodiments of the present invention will be described in detail with reference to the accompanying drawings.

First Embodiment

Figure 1:
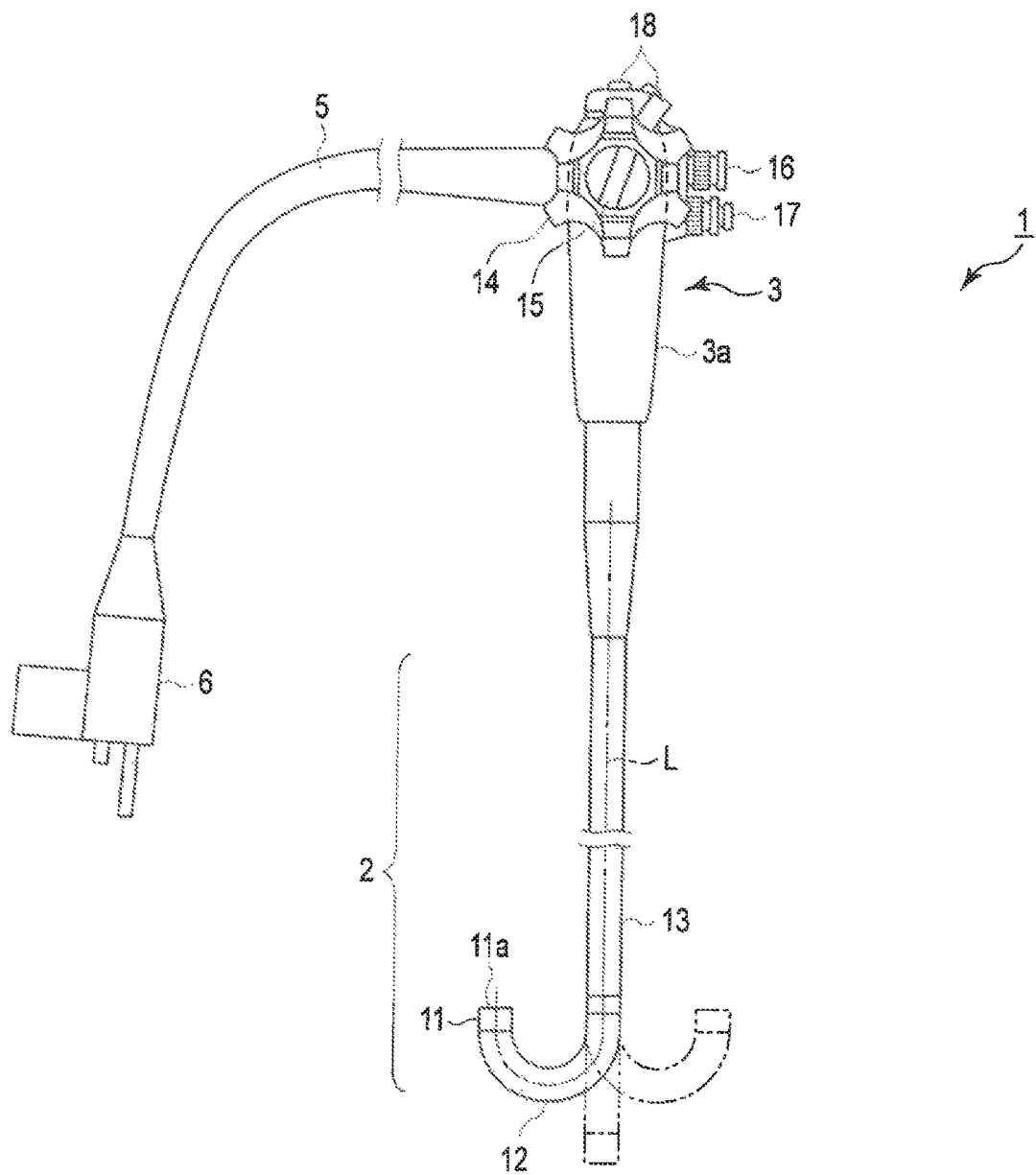
FIG. 1 is a view showing an outer structure of an endoscope main body according to a first embodiment.

FIG. 1 shows how an endoscope main body of the first embodiment looks like.

An endoscope 1 comprises a elongate insertion section (insertion device) 2 to be inserted into a cavity or a lumen, and an operation section 3 coupled to the proximal side of the insertion section 2 and configured to operate the endoscope 1. The endoscope 1 of the present embodiment is applicable to an endoscope used for observing the interior of a living body and also to an endoscope used for observing the interior of a metal pipe, an internal combustion engine or the like (a so-called industrial endoscope). In the embodiments described below, the hardness and resiliency are intended to mean as follows: The "hardness" means difficult deflection when an external force is applied, and the "resiliency" is the property to return to the original shape (straight state) of a spiral tube from a force-applied deformed state. The "initial tension" is tension (tight contact force) acting between the adjacent turns of an element wire when the element wire is spirally wound. The hardness and resiliency can be varied by controlling the initial tension.

The insertion section 2 includes: a distal end portion 11, which is made of a hard member in which an imaging optical system of an imaging section, an illumination window and others are arranged; a bendable portion 12 continuous with the proximal side of the distal end portion 11 and actively bendable; and a soft flexible tube 13 continuous with the bendable portion 12 and connected to an operation section main body 3a. Depending upon the purpose for which the endoscope is used, the insertion section 2 contains a forceps channel into which a treatment instrument is inserted, an air/water passage (tube), and the like. Openings of these structural elements are formed in the distal end face 11a of the distal end portion 11.

The bendable portion 12 has a known structure in which a plurality of annular bending pieces (not shown) are coupled to one another, with their joints rotatable. The joints of each pair of adjacent bending pieces comprises it with at least direction at right angles in turn. A plurality of wires (not shown) connected to the bending piece at the distal end are connected to angle knobs 14 and 15 provided for the operation section 3. When the angle knobs 14 and 15 are rotated, the wires are pulled and the bendable portion 12 is actively bent.

The operation section 3 includes an operation section main body 3a which has such a rectangular parallelepiped shape as can be easily held with one hand of the operator. A universal cable 5 is connected to an upper portion of the side face of the operation section main body 3a, and the proximal side of the bendable portion 12 is connected to the lower end of the operation section main body 3a. The operation section 3 and the universal cable 5 is substantially L-shaped. The universal cable 5 includes an imaging/control signal cable (not shown), a power supply cable (not shown), a light guide (not shown) for guiding illumination light, and the like, which are bundled together and covered with a resin coating member. A connector terminal 6 is at the distal end of the universal cable 5. The connector terminal 6 is connected, at least, to an image processing unit and a light source unit (neither of which is shown). The endoscope 1 is provided with such system structures as a monitor and an input device. If necessary, the endoscope 1 is provided with a pump unit which is used for supplying air and water and for suction, a treatment instrument, and the like.

On the front face of the operation section main body 3a, two angle knobs 14 and 15, used for bending the bendable portion 12, are coaxially stacked.

On the side face portion opposite to that on which the universal cord 5 is provided, a suction switch 16 and an air/water supply switch 17 are juxtaposed at such positions as enable easy operation of the switches. On the top face of the operation section main body 3a, photographing switches 18, including a shutter switch used for photographing an endoscopic image by means of an imaging optical system, are arranged.

The angle knobs 14 and 15 are specifically a UD knob (first operation portion) 14 which is rotated to bend the bendable portion 12 in the up/down direction (first axial direction) and an RL knob (second operation portion) 15 which is rotated to bend the bendable portion 15 in the right/left direction (second axial direction). In the present embodiment, the angle knobs are manually-operable knobs. They may be replaced with motor switches for bending the bendable portion 12 using a driving source such as a motor.

The structure of the flexible tube 13 will be described.

Figure 2:
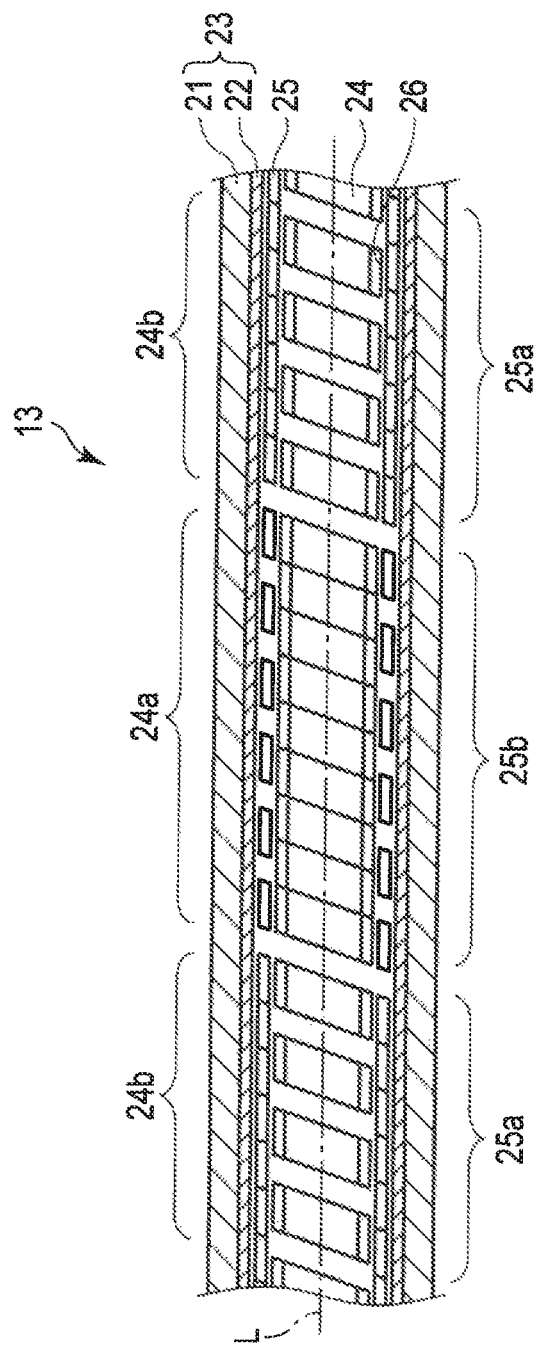
FIG. 2 is a view showing a longitudinal section illustrating a flexible tube of the first embodiment.
Figure 3:
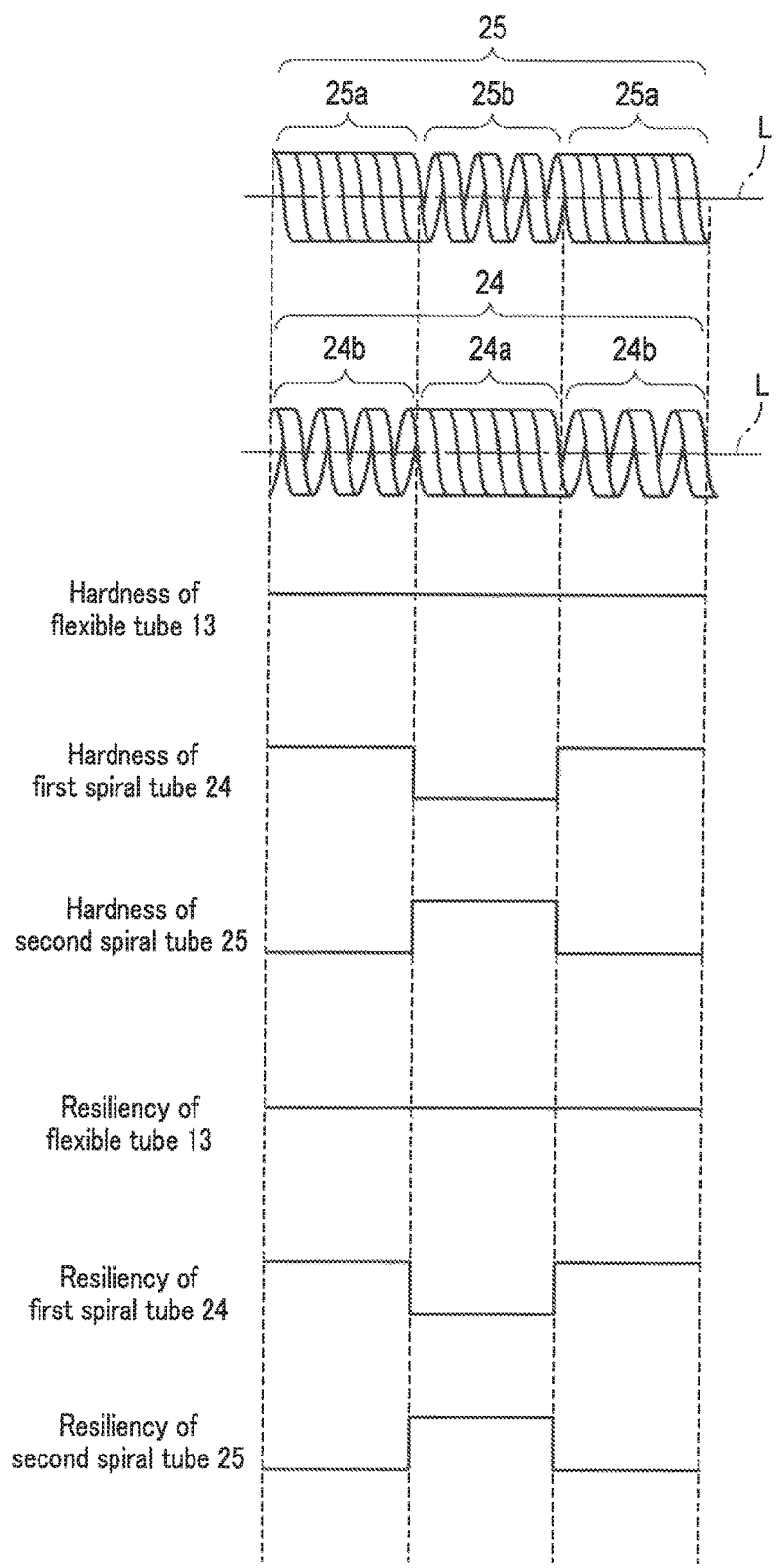
FIG. 3 illustrates how the positional relationships between a side face of a first spiral tube and a side face of a second spiral tube are in the first embodiment, and also illustrates how the hardness and resiliency of the flexible tube are.
Figure 4:
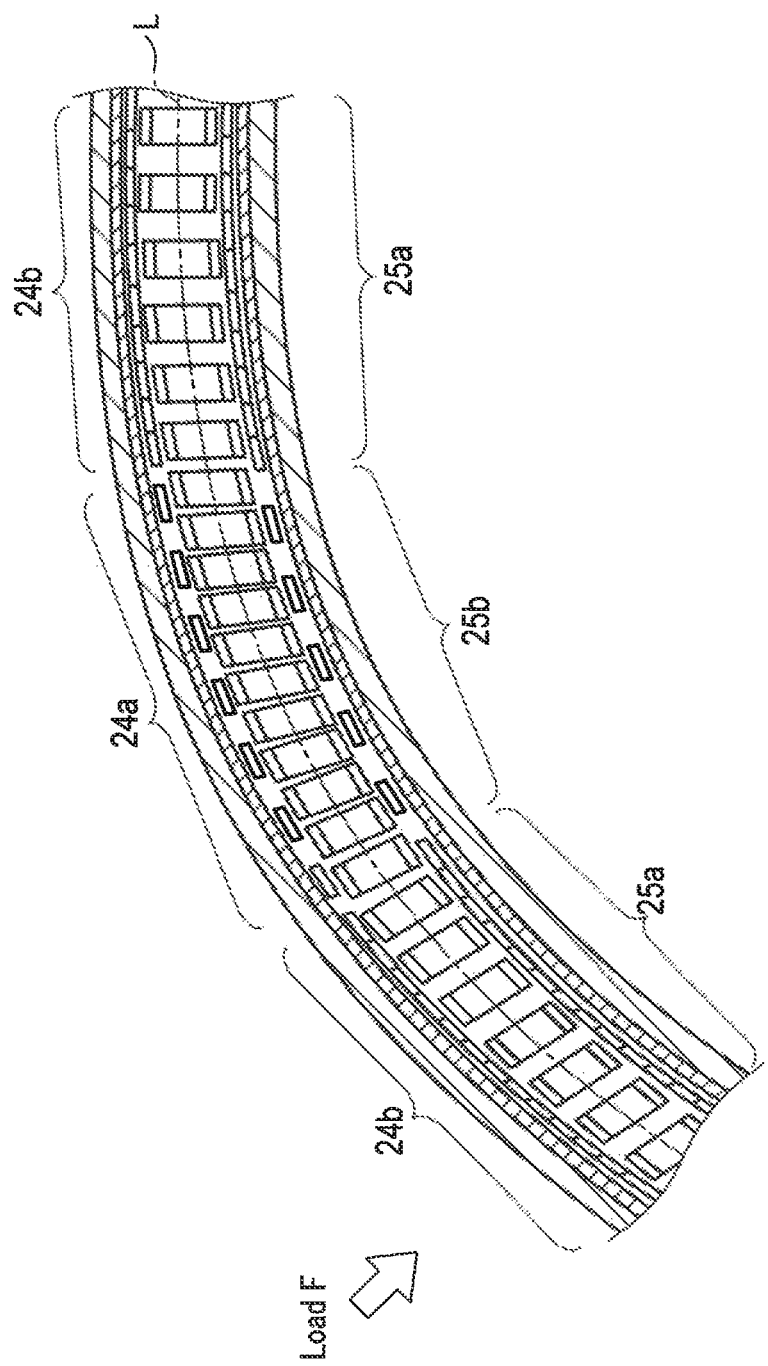
FIG. 4 is a cross-sectional view showing the first spiral tube and second spiral tube of the first embodiment bend when they are fitted in such a manner as to complement hardness.
Figure 6:
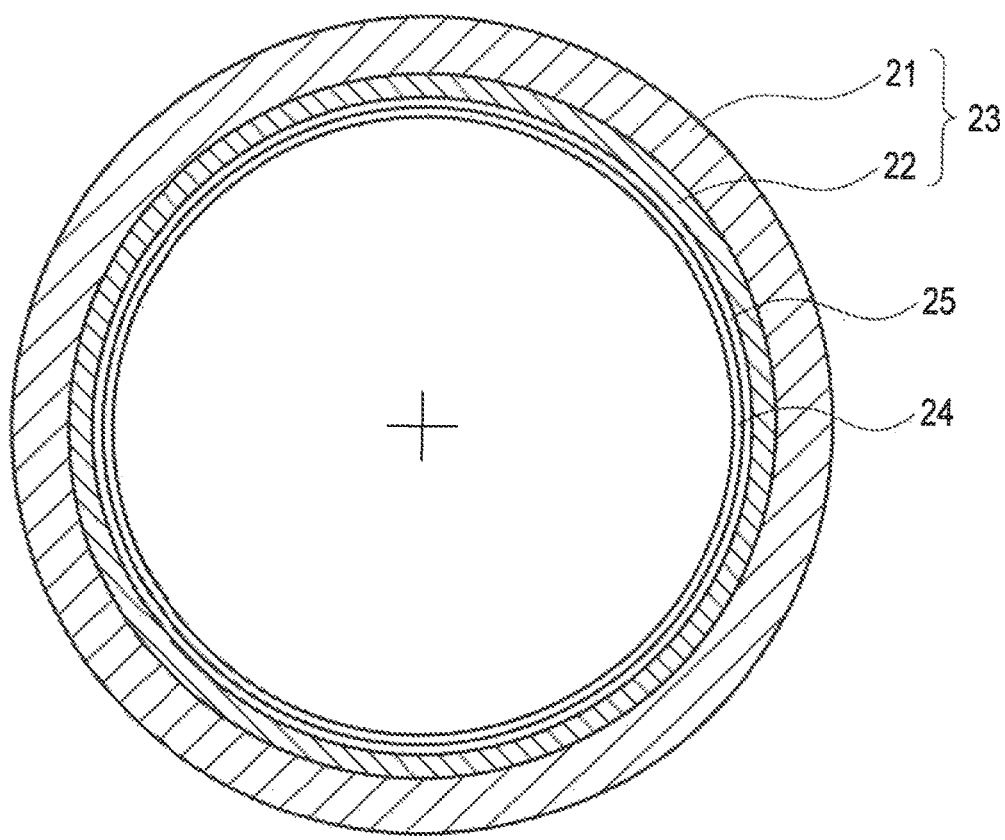
FIG. 6 is a view showing a cross-sectional structure of a flexible tube of the first embodiment in which the first spiral tube and the second spiral tube are arranged with their central axes along a common line.

FIG. 2 is a sectional view of a flexible tube of the present embodiment. FIG. 3 illustrates positional relationships between a side face of a first spiral tube and a side face of a second spiral tube, and also illustrates how the hardness and resiliency of the flexible tube are FIG. 4 is a sectional view illustrating how the first spiral tube 24 and the second spiral tube 25 bend when they are fitted in such a manner as to complement hardness. FIG. 5A illustrates how the first spiral tube 24 or the second spiral tube 25 bends. FIG. 5B illustrates how the first spiral tube 24 and the second spiral tube 25 bend when they are fitted with each other. FIG. 6 is a cross section of the flexible tube 13 in which the first spiral tube 24 and the second spiral tube 25 are fitted with their longitudinal central axes (longitudinal axes) L along a common line.

Normally, the flexible tube 13 follows the bendable portion 12 at the time of insertion into a lumen, bends in accordance with the flexures of the lumen, and transmits a propulsion force to the inserted distal end portion 11.

As shown in FIG. 2, the flexible tube 13 is hollow and contains wires used for bending operations, a light guide (a fiber cable) used for guiding illumination light, and a signal cable used for transmitting imaging signals. The flexible tube 13 may also contain a forceps channel and an air/water passage (tube), depending upon the design specifications.

The flexible tube 13 has a laminated structure including a bendable inner spiral tube (first spiral tube) 24, a bendable outer spiral tube (second spiral tube) 25, a reticulated tube 23 covering the outer face of the outer spiral tube 25, and an outer sheath 22 which is an elastic resin tube covering the outer face of the reticulated tube 23 in a liquid-tight manner. The reticulated tube 23 and the outer sheath 22 form outer layers with respect to the spiral tubes 24 and 25.

The first spiral tube 24 and the second spiral tube 25 are fitted with each other in such manner that they are in contact with each other or define a very narrow gap therebetween. Even when the first spiral tube 24 and the second spiral tube 25 expand or contract differently, they can smoothly slide on each other. At least one surface of each of the first and second spiral tubes 24 and 25 may be subjected to a treatment for reducing the friction coefficient. (For example, the surface may be coated with a material having a low friction coefficient or may be provided with fine dot-like projections.)

The first and second spiral tubes 24 and 25 change in total length in the longitudinal direction when an external force, such as a bending force, is applied thereto. The first and second spiral tubes 24 and 25 are fixed at their distal end portions and proximal end portions, together with the reticulated tube 23 and the outer sheath 22, by means of soldering, adhesion, laser welding or the like. Restricted by the outer layers, the spiral tubes 24 and 25 expand and contract and thereby absorb a length change, and the flexible tube 13 is prescribed total length in the longitudinal direction. Without reference to the states (i.e., a straight state and a bent state), the total length of the flexible tube 13, defined between the distal end and the proximal end, is substantially constant.

Each of the first spiral tube 24 and the second spiral tube 25 is a combination of densely wound portions (closely wound portions) 24a, 25a and loosely wound portions 24b, 25b, which have respective lengths. Each densely wound portion is a portion where a band-like long metal plate 26 is spirally wound to form a tube, with its adjacent turns in tight contact with each other. Each loosely wound portion is a portion where the metal plate 26 is spirally wound with its adjacent turns away from each other by a predetermined distance.

In the example shown in FIG. 3, the densely wound portions 24a, 25a and the loosely wound portions 24b, 25b are alternately arranged.

With the metal plate wound as above, the first and second spiral tubes 24 and 25 are under similar initial tensions acting along the central axis L in the longitudinal direction (or longitudinal axis). Preferably, the initial tension of densely wound portion 24a and the initial tension of densely wound portion 25a are substantially equal to each other. Depending upon the design, the initial tensions may be different. When the first spiral tube 24 and the second spiral tube 25 are fitted with each other, the plate winding direction of the first spiral tube 24 and the plate winding direction of the second spiral tube 25 may be the same or different from each other.

As shown in FIGS. 3 and 4, when the second spiral tube 25 is fitted around the first spiral tube 24, the loosely wound portions 24b of the first spiral tube 24 are opposed to the densely wound portions 25a of the second spiral tube 25, and the densely wound portions 24a of the first spiral tube 24 are opposed to the loosely wound portions 25b of the second spiral tube 25. The second spiral tube 25 is fitted around the first spiral tube 24, the loosely wound portions 24b of the first spiral tube 24 and the densely wound portions 25a of the second spiral tube 25 are arranged such that the longitudinal centers are at the same positions. In this example, the loosely wound portions 24b of the first spiral tube 24 and the densely wound portions 25a of the second spiral tube 25 have substantially the same length, as viewed in the longitudinal direction. That is, the loosely wound portions 24b are precisely covered with the densely wound portions 25a. When the first spiral tube 24 and the second spiral tube 25 are fitted with each other, the plate winding direction of the first spiral tube 24 and the plate winding direction of the second spiral tube 25 may be the same or different from each other.

As shown in FIG. 3, the hardness and resiliency of the densely wound portions and those of the loosely wound portions are indicated as a pulse shape. In the state where the first spiral tube 24 and the second spiral tube 25 are fitted with each other, densely wound portions 24a and loosely wound portions 25b are combined in such a manner as to compensate the hardness difference and the resiliency difference, and loosely wound portions 24b and densely wound portions 25a are combined likewise. In the present embodiment, the first spiral tube 24 and the second spiral tube 25 have the same hardness and resiliency characteristic. With the above arrangement, the hardness and resiliency characteristic of the flexible tube 13 are constant.

As shown in FIG. 5A, if only the first spiral tube 24 is bent, it is bent like a multi-joint structure, because the densely wound portions (which are hard to bend) and the loosely wound portions (which are easy to bend) are alternately arranged. In contrast, as shown in FIG. 5B, the flexible tube 13 is bent like an arc having the same curvature, because the first spiral tube 24 and the second spiral tube 25 are fitted with each other in such a manner as to complement or compensate the hardness.

As described above, according to the present embodiment, the densely wound portions 25a of the second spiral tube 25 are opposed to the loosely wound portions 24b of the first spiral tube 24 in such a manner as to complement or compensate the hardness. Accordingly, the hardness of the flexible tube 13 is substantially uniform. Unlike the case where the first spiral tube 24 is bent only at the loosely wound portions 24b, the flexible tube 13 is bent uniformly. For example, when the flexible tube 13 is made to pass through a flexure of the large intestine, it bends smoothly like an arc, as shown in FIG. 5B.

In addition, the resiliency characteristic of the flexible tube 13 is made uniform by arranging the densely wound portions 25a of the second spiral tube 25 to be opposed to the low-resiliency loosely wound portions 24b of the first spiral tube 24.

After passing through a flexure, the flexible tube 13 can easily return to the original straight state because of the resiliency of the densely wound portions 24a of the first spiral tube 24 and the resiliency of the densely wound portions 25a of the second spiral tube 25. Without reference to the portion of the flexible tube 13 which is located at a flexure of the intestine, the flexible tube 13 provides desirable resiliency, and the intestine can be easily made straight.

In the present embodiment, as depicted in the cross section of the flexible tube 13 shown in FIG. 6, the first spiral tube 24 and the second spiral tube 25 are fitted with their longitudinal central axes L along a common line. With this structure, when a load F is applied and the flexible tube 13 is bent, as shown in FIG. 4, the first spiral tube 24 and the second spiral tube 25 are integrally bent on the same axis. When the flexible tube 13 is bent vertically, horizontally or in any direction, it can be bent like a smooth arc having the same curvature.

Second Embodiment

A flexible tube of the second embodiment will be described.

Figure 7:
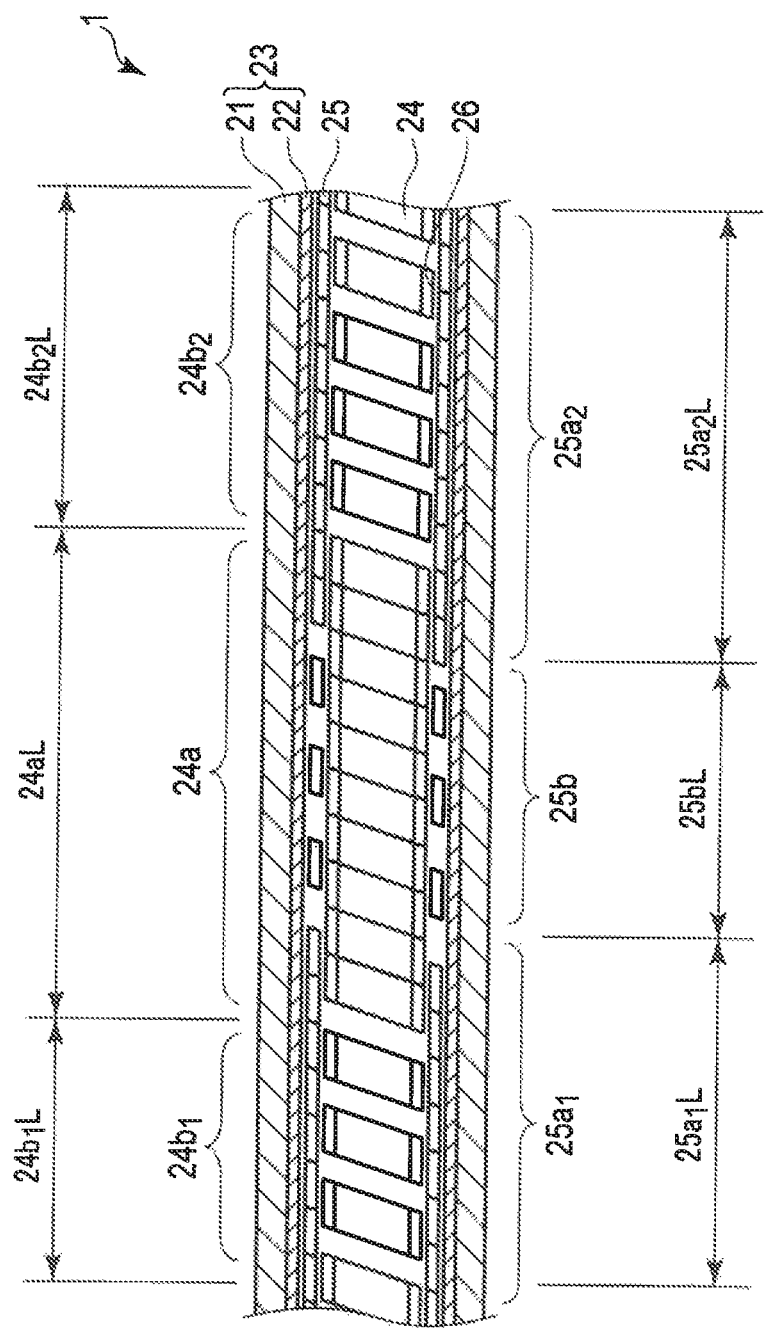
FIG. 7 is a view showing a cross-sectional structure of a flexible tube of the second embodiment.
Figure 8:
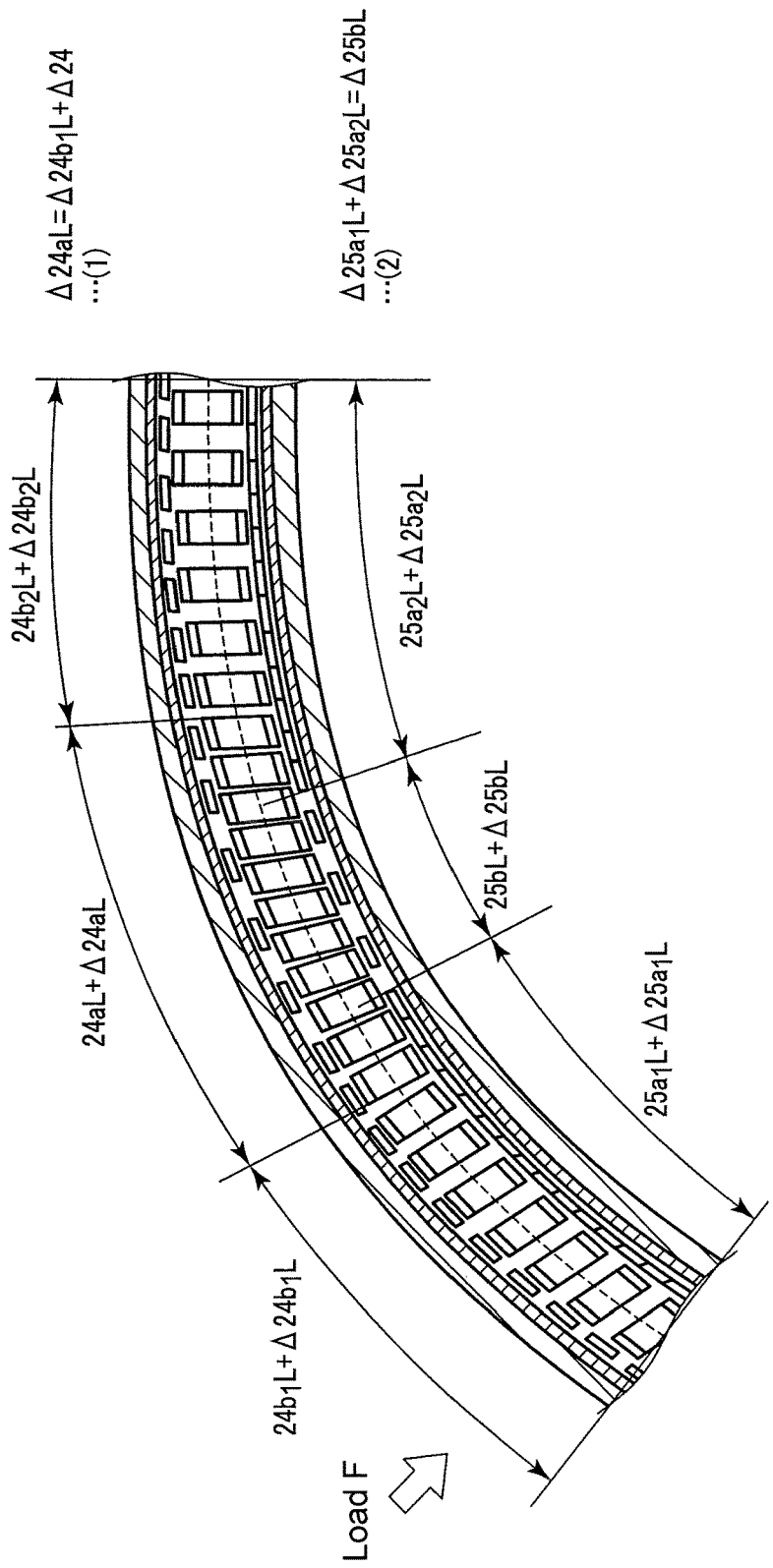
FIG. 8 is a cross-sectional view showing the flexible tube of the second embodiment bends.

FIG. 7 shows a sectional structure of the flexible tube 13 of the second embodiment. FIG. 8 is a sectional view illustrating how the flexible tube 13 bends where the first spiral tube 24 and the second spiral tube 25 of the flexible tube 13 are fitted in such a manner that the hardness of the second spiral tube 24 complements the hardness of the first spiral tube 25.

In the present embodiment, the densely wound portions 25a of the second spiral tube 25 are longer than the loosely wound portions 24b of the first spiral tube 24, as measured in the longitudinal axis (central axis L). The flexible tube 13 is featured in that each densely wound portion 25a of the second spiral tube 25 covers not only the corresponding loosely wound portion 24b of the first spiral tube 24 but also the densely wound portions 24a on the respective sides of that loosely wound portion 24b. Since the other structures are similar to those described in connection with the first embodiment, a description of them will be omitted herein.

As shown in FIG. 7, in the present embodiment, the lengths 25a1L and 25a2L of the densely wound portions 25a1 and 25a2 of the second spiral tube 25 are greater than the lengths 24b1L and 24b2L of the loosely wound portions 24b1 and 24b2 of the first spiral tube 24. When the loosely wound portions 24b of the first spiral tube 24 are arranged on the densely wound portions 25a of the second spiral tube 25, the centers of the densely wound portions of the second spiral tube are at the centers of the loosely wound portions, as viewed in the longitudinal direction.

As can be seen from this, the lengths of the densely wound portions 25a1 and 25a2 of the second spiral tube 25 are adjusted such that densely wound portions 25a1 and 25a2 cover not only the loosely wound portions 24b of the first spiral tube 24 but also the densely wound portions 24a on the respective sides of the loosely wound portions 24b. Conversely, the length 24aL of the densely wound portion 24a of the first spiral tube 24 is set to be greater than the length 25bL of the loosely wound portion 25b of the second spiral tube 25, and the densely wound portion 25a of the second spiral tube 25 covers the densely wound portions 24a of the first spiral tube 24 as well. That is, each densely wound portion of one spiral tube overlaps the end portions of densely wound portions of the other spiral tube.

As described above, the flexible tube 13 of the present embodiment is fixed at both ends, namely, at the distal end where it is connected to the bendable portion and at the proximal end where it is connected to the operation section of the endoscope, and the first and second spiral tubes 24 and 25 are slidable inside the outer layers when the first and second spiral tubes 24 and 25 expand and contract. As shown in FIG. 8, when the flexible tube 13 is bent, the densely wound portion 24a of the first spiral tube 24 expands by Δ24aL in the longitudinal direction of the central axis of the flexible tube 13. On the other hand, the loosely wound portions 24b1 and 24b2 of the first spiral tube 24 absorb the expansion of the densely wound portion 24a of the first spiral tube 24, and contract by Δ24b1L and Δ24b2L in the longitudinal direction of the central axis of the flexible tube 13.

Likewise, the densely wound portions 25a1 and 25a2 of the second spiral tube 25 expand by Δ25a1L and Δ25a2L, and the loosely wound portion 25b of the second spiral tube 25 absorbs the expansions and contracts by Δ25bL.

The length 25aL of the densely wound portion 25a of the second spiral tube 25 is set to be greater than the length 24bL of the loosely wound portion 24b of the first spiral tube 24. In other words, the end portions of the densely wound portion 25a of the second spiral tube 25 overlap the end portions of the densely wound portions 24a of the first spiral tube 24. With this structure, the loosely wound portion 24b of the first spiral portion 24b is covered with the densely wound portion 25a of the second spiral tube 25 at all times, regardless of whether the flexible tube 13 is straight or bent. Hence, the loosely wound portion 24b of the first spiral tube 24 does not overlap the loosely wound portion 25b1 or 25b2 of the second spiral tube 25.

On the other hand, if a load (bending force) is applied locally to the loosely wound portion 24b1 or 24b2 of the first spiral tube 24, the loosely wound portion 24b1 or 24b2 of the first spiral tube 24 is concentratedly bent. If the loosely wound portion 24b1 or 24b2 of the first spiral tube 24 is bent in this way, it may extend in the longitudinal direction. To cope with such extension, it is preferable that the length of the loosely wound portion 24b1 or 24b2 of the first spiral tube 24 is determined such that the loosely wound portion 24b1 or 24b2 is covered with the densely wound portion 25b1 or 25b2 of the second spiral tube 25.

The present embodiment has advantages similar to those of the first embodiment described above. That is, the loosely wound portions and densely wound portions of the spiral tubes are arranged such that the hardness and resiliency are complemented or compensated. Since the hardness of the flexible tube can be made substantially uniform, it can bend smoothly like an arc having the same curvature. In addition, the resiliency of the flexible tube is made uniform, and the flexible tube can easily return to the original straight state.

In the first embodiment described above, the loosely wound portions 24b of the first spiral tube 24 may be covered with the loosely wound portions 25b of the second spiral tube 25. To prevent this, special attention is paid to the positional relationships between the loosely wound portions 24b of the first spiral tube 24 and the densely wound portions 25a of the second spiral tube 25 when the flexible tube 13 is assembled. In the present embodiment, the densely wound portion 25a of the second spiral tube 25 covers the densely wound portion 24a of the first spiral tube 24 at all times. Even if a manufacturing error occurs at the time of assembly, the loosely wound portion 25b of the second spiral tube 25 never fails to be covered with the densely wound portion 25a of the second spiral tube 25.

Third Embodiment

A flexible tube of the third embodiment will be described.

FIG. 9 illustrates how the positional relationships between a side face of a first spiral tube 24 and a side face of a second spiral tube 25 are in the flexible tube 13 of the third embodiment, and also illustrates relationships between the hardness and resiliency of the flexible tube 13 and the hardness and resiliency of the spiral tubes 24 and 25.

In the flexible tube 13 of the present embodiment, the length of the structure in which the loosely wound portions 24b of the first spiral tube 24 are covered with the densely wound portions 25a of the second spiral tube 25 and the hardness and resiliency of the loosely wound portions 24b are compensated is not the total length of the flexible tube, as in the first embodiment, but is limited to a length determined from the distal end portion 11 of the insertion section 2. Since the other structures are similar to those described in connection with the first embodiment, a description of them will be omitted herein.

In general, the flexible tube 13 is not entirely inserted into a lumen, and the length of a portion to be inserted into the lumen of an observation target corresponds to the distance (length) between the opening of the lumen and an observation portion inside the lumen. Therefore, the above-mentioned structure, in which the loosely wound portion 24b of the first spiral tube 24 is covered with the densely wound portion 25a of the second spiral tube 25 to complement the hardness and resiliency, is applied to the portion determined by subtracting the length of a flexure from the above-mentioned length. Where the present embodiment is anatomically applied to a large-intestine endoscope, the length of the large intestine is generally said to be approximately 70 cm after insertion of the large-intestine endoscope. Therefore, the distance to a deep portion of the large intestine (a portion close to the stomach) can be regarded as approximately 90 cm in consideration of the lengths of the flexures. Where the endoscope has an insertion section which is 90 cm long, a reliable insertion property and operation are ensured.

The present embodiment is featured in that approximately 90 cm from the distal end portion 11 of the insertion section 2 is regarded as an insertion length and the structure in which the loosely wound portion 24b of the first spiral tube 24 is covered with the densely wound portion 25a of the second spiral tube 25 is applied to that portion of the flexible tube 13 determined after subtraction of the lengths of the flexures.

According to the present embodiment, the flexible tube 13 includes a tube portion which is to be inserted and in which the densely wound portions 25a of the second spiral tube 25 are opposed to the loosely wound portions 24b of the first spiral tube 24 in such a manner as to complement or compensate the hardness. Since such a tube portion has substantially uniform hardness, it can bend like a smooth arc. In addition, the resiliency characteristic of the tube portion is made uniform by arranging the densely wound portions 25b of the second spiral tube 25 to be opposed to the low-resiliency loosely wound portions 24b of the first spiral tube 24. Since the loosely wound portions 24b are provided with resiliency similar to that of the densely wound portions 25b, the tube portion can easily return to the original straight state.

In the present embodiment, the densely wound portions 25a of the second spiral tube 25 are arranged only in a tube portion corresponding to the necessary length, and loosely wound portions are arranged in the other tube portions. As a result, the manufacturing cost of the second spiral tube 25 can be reduced. In addition, the weight of the endoscope can be reduced, and the operator's fatigue can be alleviated.

In connection with the flexible tubes of the first to third embodiments, reference was made to the double tube structure in which the second spiral tube 25 is fitted around the first spiral tube 24. However, the present invention is not limited to this. The structure of the present invention is applicable to a flexible tube 13 in which three or more spiral tubes are fitted with one another. In this case, in a unit portion of the flexible tube 13, each spiral tube includes a densely wound portion and a loosely wound portion, and a loosely wound portion of one spiral tube is covered with a densely wound portion of another spiral tube.

The flexible tubes of the first to third embodiments described above are employed in an endoscope (insertion section), which is an insertion device. The insertion device may be configured as an insertion section 2 and includes at least a flexible tube 13 and a bendable portion 12.

The present invention can provide a flexible tube which can exhibit desirable resilient property and enables an easy insertion operation by reinforcing a loosely wound portion of a first spiral tube with a densely wound portion of a second spiral tube, so that the hardness and resiliency of the loosely wound portion are complemented and the densely wound portion and the loosely wound portion can bend with the same curvature. The present invention can also provide an insertion device employing such a flexible tube.

A flexible tube according to the present invention comprises a plurality of spiral tubes overlaid and fitted with one another, with their central axes along a common line, each of the spiral tubes being fixed at both ends and formed of a spirally wound element wire, the spiral tubes including a first spiral tube and a second spiral tube, each of the first spiral tube and the second spiral tube including at least one densely wound portion and a loosely wound portion located at least at one end of the densely wound portion, the loosely wound portion of the first spiral tube being overlaid and fitted with the densely wound portion of the second spiral tube.

The first to third embodiments described above have the following advantages:

(1) Each densely wound portion 25a of the second spiral tube 25 has substantially the same length as each loosely wound portion 24b of the first spiral tube 24, as measured in the longitudinal direction. Where the densely wound portion 25a and the loosely wound portion 24b are formed (wound) to have substantially the same length, the loosely wound portion 24b can be covered with the densely wound portion 24b with the same dimensions. Where the densely wound portion 25a of the second spiral tube 25 is formed (wound) to be longer than the loosely wound portion 24b of the first spiral tube 24, the densely wound portion 25a can cover not only the loosely wound portions 24b but also end portions of the densely wound portions 24a adjacent to the loosely wound portion 24b. Where the end portions of the densely wound portions 24a and 25a overlap each other, the loosely wound portion 24b of the first spiral tube 24 does not protrude from the overlap of the densely wound portion of the second spiral tube 13.

(2) Since the densely wound portion of the second spiral tube is opposed to the loosely wound portion of the first spiral tube, the following advantages are attained:

a) The densely wound portion of the second spiral tube is opposed to the loosely wound portion of the first spiral tube, and the hardness of the loosely wound portion can be complemented or compensated. With this structure, the hardness of the flexible tube is made substantially uniform, and the flexible tube can bend like an arc having the same curvature. In addition, since the resiliency of the loosely wound portion of the first spiral tube is complemented with the resiliency of the densely wound portion of the second spiral tube, and the loosely wound portion is provided with resiliency similar to that of the densely wound portion, the flexible tube can easily return to the original straight state.

b) The first spiral tube and the second spiral tube are coaxial and have the same central axis L. With this structure, the flexible tube provides the same resiliency when it is bent in any direction.

c) The first spiral tube and the second are fitted with each other. When the flexible tube is bent, both the first spiral tube and the second spiral tube are deformed. As a result, the flexible tube provides uniform resiliency without reference to the degree of deformation of the flexible tube.

d) When the flexible tube is assembled, the assembler can visually confirm how the positional relationship between the first spiral tube and the second spiral tube is in the longitudinal direction. Since the densely wound portion of the second spiral tube can be reliably arranged for the loosely wound portion of the first spiral portion, the flexible tube can be assembled easily.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube comprising:
    a first spiral tube including:
        a first densely wound portion in which a first element wire is wound such that adjacent turns are in tight contact with each other with an initial tension, and
        a first loosely wound portion in which the first element wire is wound such that adjacent turns are spaced from each other by a constant distance, the first densely wound portion and the first loosely wound portion alternating in a direction of a central axis of the first spiral tube, and a second spiral tube including:
- a second densely wound portion in which a second element wire is wound such that adjacent turns are in tight contact with each other with an initial tension, and
- a second loosely wound portion in which the second element wire is wound such that adjacent turns are spaced from each other by a constant distance, the second densely wound portion and the second loosely wound portion alternating in a direction of a central axis of the second spiral tube, wherein:
- the first spiral tube and the second spiral tube have an equal length in a longitudinal direction and are overlaid on each other,
- the first spiral tube is fitted in and fixed at both ends to the second spiral tube to have a positional relationship that makes:
  - the first loosely wound portion of the first spiral tube opposed to the second densely wound portion of the second spiral tube,
  - the first densely wound portion of the first spiral tube opposed to the second loosely wound portion of the second spiral tube, and
  - the central axis of the first spiral tube align with the central axis of the second spiral tube.

2. The flexible tube according to claim 1, wherein the length of the first spiral tube and the second spiral tube in the longitudinal direction is substantially constant even when the flexible tube is bent because the first spiral tube and the second spiral tube are fixed to each other at both ends, and a displacement of relative positions of the first spiral tube and the second spiral tube is restricted.

3. The flexible tube according to claim 1, wherein:
- the second densely wound portion of the second spiral tube is longer than the first loosely wound portion of the first spiral tube, and
- in the state where the first spiral tube and the second spiral tube are overlaid with each other, the second densely wound portion of the second spiral tube overlaps the first densely wound portion adjacent to the first loosely wound portion of the first spiral tube regardless of a form of the flexible tube including a bending state.

4. The flexible tube according to claim 1, wherein a structure portion in which the second densely wound portion of the second spiral tube is opposed to the first loosely wound portion of the first spiral tube has a length determined by a distance between an opening of an observation target and an observation portion.

5. The flexible tube according to claim 1, wherein the first spiral tube and the second spiral tube are spaced from each other, and
at least one of the first spiral tube and the second spiral tube includes a surface subjected to a friction coefficient-reducing treatment.

6. An insertion device having a flexible tube as defined in claim 1.

7. An endoscope having a flexible tube as defined in claim 1.

* * * * *